United States Patent
Konetzki et al.

(10) Patent No.: US 7,135,500 B2
(45) Date of Patent: Nov. 14, 2006

(54) DIHYDROXYMETHYLPHENYL DERIVATIVES, PROCESSES FOR PREPARING THEM, AND THEIR USE AS PHARMACEUTICALS

(75) Inventors: Ingo Konetzki, Warthausen (DE); Kurt Schromm, Ingelheim am Rhein (DE); Hermann Schollenberger, Ingelheim am Rhein (DE); Sabine Pestel, Biberach (DE); Andreas Schnapp, Biberach (DE); Thierry Bouyssou, Mietingen (DE); Frank Buettner, Ummendort (DE); Claudia Heine, Biberach (DE)

(73) Assignee: Boehringer Ingelheim Pharma GmbH & Co KG, Ingelheim (DE)

( * ) Notice: Subject to any disclaimer, the term of this patent is extended or adjusted under 35 U.S.C. 154(b) by 324 days.

(21) Appl. No.: 10/697,525

(22) Filed: Oct. 30, 2003

(65) Prior Publication Data
US 2004/0138307 A1    Jul. 15, 2004

Related U.S. Application Data

(60) Provisional application No. 60/434,053, filed on Dec. 17, 2002.

(30) Foreign Application Priority Data

Nov. 15, 2002    (DE)    ............... 102 53 220

(51) Int. Cl.
*A61K 31/425*    (2006.01)
*C07C 213/00*    (2006.01)

(52) U.S. Cl. ...................... 514/653; 564/365
(58) Field of Classification Search ................ 514/653; 564/365
See application file for complete search history.

(56) References Cited

U.S. PATENT DOCUMENTS 3,657,244 A * 4/1972 Mentrup et al. ............ 564/362
3,969,410 A    7/1976 Mentrup et al.
4,042,713 A    8/1977 Mentrup et al.
4,990,505 A * 2/1991 Skidmore et al. ...... 514/211.01
5,223,614 A * 6/1993 Schromm et al. ........... 544/105
2002/0022625 A1    2/2002 Walland et al.

FOREIGN PATENT DOCUMENTS

WO    WO 01/83462    11/2001

OTHER PUBLICATIONS

Goodman and Gilman's The Pharmcological Basis of Therapeutics, 6th Edition, publiashed 1980 by MacMillan Publishing Co. (NY), pp. 120-137, 153 and 154.*
Remington's Pharmaceutical Sciences, 16th Edition, published 1980 by Mack Publishing Company (PA), pp. 431-435.*

* cited by examiner

*Primary Examiner*—Raymond J. Henley, III
(74) *Attorney, Agent, or Firm*—Michael Morris; Anthony P. Bottino; Andrea D. Small

(57) ABSTRACT

A compound of formula 1

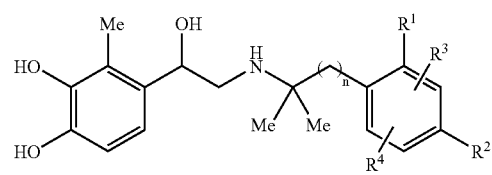

wherein the groups $R^1$, $R^2$, $R^3$, and $R^4$ may have the meanings given in the claims and in the specification, processes for preparing them, and their use as pharmaceutical compositions, particularly for the treatment of inflammatory and obstructive respiratory complaints.

16 Claims, No Drawings

DIHYDROXYMETHYLPHENYL DERIVATIVES, PROCESSES FOR PREPARING THEM, AND THEIR USE AS PHARMACEUTICALS

RELATED APPLICATIONS

This application claims benefit of U.S. Ser. No. 60/434,053, filed Dec. 17, 2002, and claims priority to German Application No. 102 53 220.6, filed Nov. 15, 2002, each of which is hereby incorporated by reference in its entirety.

FIELD OF THE INVENTION

The present invention relates to compounds of general formula 1

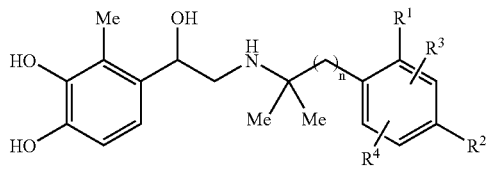

wherein the groups $R^1$, $R^2$, $R^3$, and $R^4$ may have the meanings given in the claims and in the specification, processes for preparing them, and their use as pharmaceutical compositions, particularly for the treatment of inflammatory and obstructive respiratory complaints.

BACKGROUND OF THE INVENTION

Betamimetics (β-adrenergic substances) are known from the prior art. Reference may be made, for example, to the disclosures of U.S. Pat. Nos. 4,647,563; 4,581,367; 4,378,361; 4,341,778; 3,969,410; and 3,657,244. Betamimetics may be used to good effect in a variety of therapeutic fields.

For drug treatment of diseases, it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide betamimetics which are characterized by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day. A further objective of the invention is to prepare new betamimetics which, by virtue of their long-lasting effect, can be used to prepare a drug for administration once a day for the treatment of inflammatory or obstructive respiratory complaints.

In addition to the above objectives, the present invention also sets out to provide betamimetics which are not only exceptionally potent but are also characterized by a high degree of selectivity with respect to the $β_2$-adrenoreceptor.

DETAILED DESCRIPTION OF THE INVENTION

Surprisingly it has been found that the abovementioned problems are solved by compounds of general formula 1.

Accordingly, the present invention relates to compounds of general formula 1

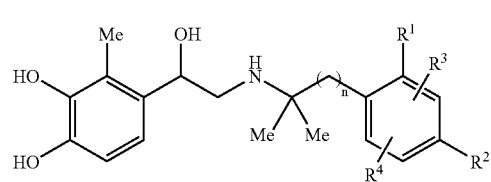

wherein:
n denotes 1, 2, or 3;
$R^1$ denotes —$C_1$–$C_4$-alkyl; and
$R^2$, $R^3$, and $R^4$, which may be identical or different, denote hydrogen, —$C_1$–$C_4$-alkyl, —OH, —O—$C_1$–$C_4$-alkyl, —$C_1$–$C_4$-alkylene-halogen, —$C_1$–$C_4$-alkylene-OH, —$C_1$–$C_4$-alkylene-O—$C_1$–$C_4$-alkyl, —$CF_3$, —$CHF_2$, —$NH_2$, —NH($C_1$–$C_4$-alkyl), —N($C_1$–$C_4$-alkyl)$_2$, halogen, —COOH, —COO—$C_1$–$C_4$-alkyl, —NHCO—$C_1$–$C_4$-alkyl, —$NHSO_2$—$C_1$–$C_4$-alkyl or —$SO_2NH_2$.

Preferred compounds of formula 1 are those wherein:
n denotes 1 or 2;
$R^1$ denotes methyl or ethyl; and
$R^2$, $R^3$, and $R^4$, which may be identical or different, denote hydrogen, methyl, ethyl, —OH, methoxy, ethoxy, —$CH_2F$, —$CH_2Cl$, —$CH_2Br$, —$CH_2CH_2F$, —$CH_2CH_2Cl$, —$CH_2CH_2Br$, —$CH_2OH$, —$CH_2CH_2OH$, —$CH_2$Omethyl, —$CH_2CH_2$Omethyl, —$CH_2$Oethyl, —$CH_2CH_2$O-ethyl, —$CF_3$, —$CHF_2$, —$NH_2$, —NHmethyl, —NHethyl, —N(methyl)$_2$, —N(ethyl)$_2$, fluorine, chlorine, bromine, —COOH, —COOmethyl, —COOethyl, —NHCO-methyl, —NHCO-ethyl, —$NHSO_2$-methyl or —$NHSO_2$-ethyl.

Particularly preferred compounds of formula 1 are those wherein:
n denotes 1 or 2;
$R^1$ denotes methyl or ethyl; and
$R^2$, $R^3$, and $R^4$, which may be identical or different, denote hydrogen, methyl, ethyl, —OH, methoxy, ethoxy, —$CH_2F$, —$CH_2CH_2F$, —$CH_2OH$, —$CH_2CH_2OH$, —$CH_2$Omethyl, —$CH_2CH_2$Omethyl, —$CH_2$Oethyl, —$CH_2CH_2$Oethyl, —$CF_3$, or —$CHF_2$.

Also of special significance according to the invention are compounds of formula 1 wherein:
n denotes 1 or 2, preferably 1;
$R^1$ denotes methyl or ethyl; and
$R^2$, $R^3$, and $R^4$, which may be identical or different, denote hydrogen, methyl, ethyl, —OH, methoxy, ethoxy, —$CF_3$, or —$CHF_2$.

Also of special significance according to the invention are compounds of formula 1 wherein:
n denotes 1 or 2, preferably 1;
$R^1$ denotes methyl or ethyl; and
$R^2$, $R^3$, and $R^4$, which may be identical or different, denote hydrogen, methyl, ethyl, —OH, or —$CF_3$.

Also particularly preferred are compounds of formula 1 wherein:

n denotes 1 or 2, preferably 1;
$R^1$ denotes methyl or ethyl; and
$R^2$, $R^3$, and $R^4$, which may be identical or different, denote hydrogen, methyl, or —OH.

Of equal importance according to the invention, finally, are compounds of formula 1 wherein:

n denotes 1 or 2, preferably 1;
$R^1$ denotes methyl or ethyl;
$R^2$ denotes hydrogen; and
$R^3$ and $R^4$ which may be identical or different, denote hydrogen, methyl, or —OH.

In the compounds of general formula 1, the groups $R^2$, $R^3$, and $R^4$ may have the same or different meanings. In the compounds the groups $R^2$, $R^3$, and $R^4$, if they do not represent hydrogen, may in each case be in the ortho-, meta-, or para-position relative to the link to the benzylic "—CH$_2$" group.

Of particular interest are compounds of formula 1 wherein $R^1$ denotes methyl and the groups $R^2$, $R^3$, and $R^4$ may have the meanings given above.

Also of particular interest are compounds of formula 1 wherein $R^1$ denotes methyl, $R^2$ denotes hydroxy, and the groups $R^3$ and $R^4$ may have the meanings given above.

Also of particular interest are compounds of formula 1 wherein n denotes 1 or 2, preferably 1, $R^3$ denotes hydrogen, and the groups $R^2$ and $R^4$ may have the meanings given above with the exception of hydrogen. In these compounds, the group $R^4$ may in each case be in the ortho-, meta-, or para-position relative to the link to the benzylic "—CH$_2$" group. Preferred compounds in this group are those wherein the group $R^4$ has the ortho configuration.

The following compounds of formula 1, for example, are of exceptional importance according to the invention:

4-{2-[1,1-dimethyl-2-(2,6-dimethyl-4-hydroxyphenyl)ethylamino]-1-hydroxyethyl}-3-methylbenzene-1,2-diol; and
4-{2-[1,1-dimethyl-2-(2,4,6-trimethylphenyl)ethylamino]-1-hydroxyethyl}-3-methylbenzene-1,2-diol.

The invention relates to the compounds of formula 1, optionally in the form of the individual optical isomers, mixtures of the individual enantiomers or racemates, in the form of the free bases, or the corresponding acid addition salts with pharmacologically acceptable acids.

By acid addition salts with pharmacologically acceptable acids are meant, for example, the salts selected from among the hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumatate, hydrotartrate, hydrooxalate, hydrosuccinate, hydrobenzoate and hydro-p-toluenesulfonate, preferably the hydrochloride, hydrobromide, hydrosulfate, hydrophosphate, hydrofumarate, and hydromethanesulfonate.

Of the abovementioned acid addition salts, the salts of hydrochloric acid, methanesulfonic acid, benzoic acid, and acetic acid are particularly preferred according to the invention.

For use according to the invention, the compounds of general formula 1 may optionally be used in the form of their individual optical isomers, mixtures of the individual enantiomers or racemates. If the compounds are used in enantiomerically pure form, the R-enantiomers are preferred. The individual enantiomers of the compounds according to the invention may be obtained from the racemates using methods known from the prior art (e.g., chromatography on chiral phases etc.).

Unless otherwise stated, the alkyl groups are straight-chained or branched alkyl groups having 1 to 4 carbon atoms. The following are mentioned by way of example: methyl, ethyl, propyl, or butyl. In some cases the abbreviations Me, Et, Prop, or Bu are used to denote the groups methyl, ethyl, propyl, or butyl. Unless otherwise stated, the definitions propyl and butyl include all the possible isomeric forms of the groups in question. Thus, for example, propyl includes n-propyl and isopropyl, butyl includes isobutyl, sec-butyl, and tert-butyl, etc.

Unless otherwise stated, the alkylene groups are branched and unbranched double-bonded alkyl bridges having 1 to 4 carbon atoms. The following are mentioned by way of example: methylene, ethylene, n-propylene, or n-butylene.

Unless otherwise stated, the term alkyloxy groups (or —O-alkyl groups) denotes branched and unbranched alkyl groups having 1 to 4 carbon atoms which are linked via an oxygen atom. Examples of these include: methyloxy, ethyloxy, propyloxy, or butyloxy. The abbreviations MeO—, EtO—, PropO—, or BuO— are used in some cases to denote the groups methyloxy, ethyloxy, propyloxy, or butyloxy. Unless otherwise stated, the definitions propyloxy and butyloxy include all possible isomeric forms of the groups in question. Thus, for example, propyloxy includes n-propyloxy and isopropyloxy, butyloxy includes isobutyloxy, sec-butyloxy, and tert-butyloxy, etc. In some cases, within the scope of the present invention, the term alkoxy is used instead of the term alkyloxy. Accordingly, the terms methoxy, ethoxy, propoxy, or butoxy may also be used to denote the groups methyloxy, ethyloxy, propyloxy, or butyloxy.

Halogen within the scope of the present invention denotes fluorine, chlorine, bromine, or iodine. Unless stated otherwise, fluorine and bromine are the preferred halogens.

The compounds according to the invention may be prepared analogously to methods already known from the prior art. Suitable methods of preparation are known, for example, from U.S. Pat. Nos. 3,969,410 and 3,657,244, each of which is incorporated by reference herein in its entirety.

The examples of synthesis described below serve to illustrate the present invention more fully. They are intended only as examples of procedure to illustrate the invention without restricting it to the subject matter described hereinafter.

EXAMPLE 1

4-{2-[1,1-dimethyl-2-(2,6-dimethyl-4-hydroxyphenyl)ethylamino]-1-hydroxyethyl}-3-methylbenzene-1,2-diol

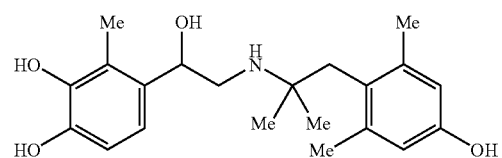

2-[1,1-dimethyl-2-(2,6-dimethylhydroxyphenyl)ethylamino]-1-(3,4-dibenzyloxy-2-methylphenyl)ethanone 14 g of 2-hydroxy-2-ethoxy-1-oxo-1-(2-methyl-3,5-dibenzyloxyphenyl)ethane and 8.5 g of 1,1-dimethyl-2-(2,6-dimethyl-4-acetyloxyphenyl)ethylamine are stirred for 3 hours at 50° C.–60° C. in 150 mL of ethanol. After cooling to 10° C., 5 g of sodium borohydride is added and the mixture is stirred for one hour. Then some acetone is added and stirring is continued for a further 30 minutes. The reaction mixture is combined with ethyl acetate, washed with water, dried with sodium sulfate, and evaporated down. The residue is dissolved in ethyl acetate and acidified with ethereal hydrochloric acid. The hydrochloride that crystallizes out is filtered off and precipitated from methanol/water. Yield: 10 g (50%) of hydrochloride; melting point: 214° C.–216° C. (decomposition).

b) 4-{2-[1,1-dimethyl-2-(2,6-dimethyl-4-hydroxyphenyl)ethylamino]-1-hydroxyethyl}-3-methylbenzene-1,2-diol 7 g of 2-[1,1-dimethyl-2-(2,6-dimethylhydroxyphenyl)ethylamino]-1-(3,4-dibenzyloxy-2-methylphenyl)ethanone hydrochloride in 125 mL of methanol is hydrogenated using 2 g of palladium on charcoal (5%). After separation of the catalyst, the solvent is distilled off. The solid that crystallizes out is stirred into acetonitrile, suction filtered, and washed. Yield: 3.5 g of hydrochloride; melting point: 182° C.–183° C. (decomposition).

EXAMPLE 2

4-[2-(1,1-dimethyl-2-o-tolylethylamino)-1-hydroxyethyl]-3-methylbenzene-1,2-diol

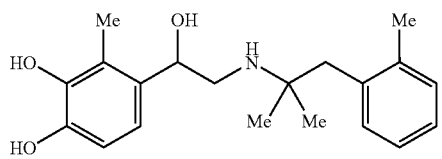

a) 2-(1,1-dimethyl-2-o-tolylethylamino)-1-(3,4-dibenzyloxy-2-methylphenyl)ethanone 36.5 g of α-bromo-3,4-dibenzyloxy-2-methylacetophenone, 14 g of 1,1-dimethyl-2-o-tolylethylamine, and 15 g of sodium carbonate are combined and refluxed for two hours in 200 mL of acetonitrile. Then the inorganic salts are filtered off and the filtrate is combined with 100 mL of water and 10 mL of concentrated hydrochloric acid. The product precipitated is suction filtered and washed. Yield: 27 g (58%) of hydrochloride; melting point: 190° C.–195° C.

b) 2-(1,1-dimethyl-2-o-tolylethylamino)-1-(3,4-dihydroxy-2-methylphenyl)ethanone 27 g of the ketone mentioned above are dissolved in 250 mL of methanol and hydrogenated with palladium (II) chloride at 60° C. and 5 bar. After the theoretically calculated amount of hydrogen has been taken up, the catalyst is filtered off and the filtrate is evaporated down. The product that crystallizes out when the solvent is distilled off is stirred with ethyl acetate, suction filtered, and washed. Yield: 15 g (83%) of hydrochloride.

For further purification, the hydrochloride may first be converted into the free base. By treating the free base with concentrated hydrochloric acid in methanol, the title compound may optionally be precipitated again as the hydrochloride. Melting point: 218° C.–225° C. (decomposition).

c) 4-[1-(1,1-dimethyl-2-o-tolylethylamino)-1-hydroxyethyl]-3-methylbenzene-1,2-diol 8 g of 2-(1,1-dimethyl-2-o-tolylethylamino)-1-(3,4-dihydroxy-2-methylphenyl)ethanone hydrochloride is placed in 125 mL of methanol and hydrogenated in the presence of 0.3 g of platinum (IV) oxide at ambient temperature and under normal pressure. The catalyst is suction filtered and the filtrate is freed from solvent. The crude product is recrystallized from ethyl acetate, filtered off, and washed. Yield: 6.5 g of hydrochloride, melting point: 166° C.–169° C.

EXAMPLE 3

4-{2-[1,1-dimethyl-2-(2,4,6-trimethylphenyl)ethylamino]-1-hydroxyethyl}-3-methylbenzene-1,2-diol

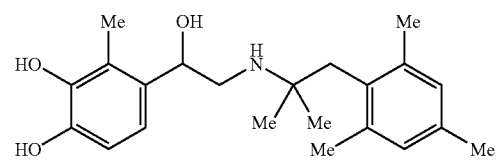

350 mg (0.86 mmol) of 1-(3,4-bis-benzyloxy-2-methylphenyl)-2-ethoxy-2-hydroxyethanone and 198 mg (1.03 mmol) of 1,1-dimethyl-2-(2,4,6-trimethylphenyl)ethylamine were dissolved in 3 mL of ethanol and heated to 80° C. for 30 minutes in the presence of some molecular sieve. After cooling to ambient temperature, 33 mg (0.86 mmol) sodium borohydride was added and the mixture was stirred for 1 hour. The reaction mixture was combined with ethyl acetate and washed with sodium hydrogen carbonate solution. Then the organic phase was freed from solvent and chromatographed. In order to cleave the benzyl protecting groups, the ethanolamine-thus-obtained (364 mg) was dissolved in methanol, combined with 150 mg of Pearlman's catalyst, and hydrogenated at ambient temperature and under normal pressure. The reaction mixture was filtered through CELITE® filter agent and evaporated down. Chromatographic purification of the residue with dichloromethane and methanol as eluent yielded the target compound as a beige solid. Yield: 179 mg (29%); mass spectrometry: [M+H]$^+$ =391.

It has been found that the compounds of general formula 1 are characterized by their versatility of use in the therapeutic field. Particular mention should be made of those applications for which the compounds of formula 1 according to the invention are preferably used by virtue of their pharmaceutical effectiveness as betamimetics. These include, for example, the treatment of inflammatory and obstructive diseases of the respiratory tract, preferably the treatment of asthma or chronic obstructive pulmonary disease (COPD), the inhibition of premature labor in midwifery (tocolysis), the restoration of sinus rhythm in the heart in atrioventricular block, as well as the elimination of bradycardic heart rhythm disorders (antiarrhythmic), the treatment of cardiovascular shock (vasodilatation and increasing the cardiac output), as well as the treatment of itching and irritations of the skin.

In one aspect, the present invention relates to the use of the compounds of general formula 1 as pharmaceutical compositions. In another aspect, the present invention relates to the use of the compounds of general formula 1 for preparing a pharmaceutical composition for the treatment of diseases wherein therapeutically effective doses of a betamimetic may provide a therapeutic benefit. It is particularly preferable to use compounds of general formula 1 for preparing a pharmaceutical composition for the treatment of inflammatory and obstructive respiratory complaints, particularly preferably asthma or COPD, for inhibiting premature labor in midwifery (tocolysis), for restoring sinus rhythm in the heart in atrioventricular block, for eliminating bradycardic heart rhythm disorders (antiarrhythmic), for treating cardiovascular shock (vasodilatation and increasing the cardiac output), as well as for treating itching and irritations of the skin. It is particularly preferred according to the invention to use compounds of general formula 1 to prepare a pharmaceutical composition for the treatment of inflammatory and obstructive respiratory complaints, most preferably for treating asthma or COPD. Also of particular importance is the abovementioned use of compounds of general formula 1 for preparing a pharmaceutical composition for once-a-day treatment of inflammatory and obstructive respiratory complaints, most preferably for once-a-day treatment of asthma or COPD.

The compounds of general formula 1 may be used on their own or combined with other active substances of formula 1 according to the invention. The compounds of general formula 1 may optionally also be combined with other pharmacologically active substances. These include, in particular, anticholinergics, optionally other betamimetics, antiallergic agents, PDE-IV inhibitors, PAF-antagonists, leukotriene-antagonists, and steroids and combinations of these active substances.

Examples of anticholinergics which may be mentioned include ipratropium bromide, oxitropium bromide, and particularly tiotropium bromide. Pharmaceutical combinations contain tiotropium bromide, optionally in the form of one of its solvates or hydrates, as an additional active substance, as well as the compounds of formula 1 according to the invention are particularly preferred. Tiotropium bromide is most preferably used in the form of its monohydrate, particularly in the form of its crystalline monohydrate. This crystalline monohydrate is described in detail in WO 02/30928 (see U.S. Patent Application Publication No. 2003/10171586 which is incorporated by reference herein in its entirety).

Within the scope of the present invention, the corticosteroids which may optionally be used in conjunction with the compounds of formula 1 may be compounds selected from among flunisolide, beclomethasone, triamcinolone, budesonide, fluticasone, mometasone, ciclesonide, rofleponide, and dexamethasone. Preferably, within the scope of the present invention, the corticosteroids are selected from among flunisolide, beclomethasone, triamcinolone, budesonide, fluticasone, mometasone, ciclesonide, and dexamethasone, while budesonide, fluticasone, mometasone, and ciclesonide are important and budesonide and fluticasone are particularly important. In some cases, within the scope of the present patent application, the term steroids is used on its own instead of the word corticosteroids. Any reference to steroids within the scope of the present invention includes a reference to salts or derivatives which may be formed from the steroids. Examples of possible salts or derivatives include: sodium salts, sulfobenzoates, phosphates, isonicotinates, acetates, propionates, dihydrogen phosphates, palmitates, pivalates, or furoates. In some cases, the corticosteroids may also occur in the form of their hydrates.

Within the scope of the present invention, the term dopamine agonists, which may optionally be used in conjunction with the compounds of formula 1, denotes compounds selected from among bromocriptine, cabergoline, alpha-dihydroergocryptine, lisuride, pergolide, pramipexol, roxindole, ropinirole, talipexole, terguride, and viozan. It is preferable within the scope of the present invention to use, as combination partners with the compounds of formula 1 dopamine agonists selected from among pramipexol, talipexole, and viozan, pramipexol being of particular importance. Any reference to the abovementioned dopamine agonists also includes, within the scope of the present invention, a reference to any pharmacologically acceptable acid addition salts and hydrates thereof which may exist. By the physiologically acceptable acid addition salts thereof which may be formed by the abovementioned dopamine agonists are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid.

Examples of antiallergic agents which may be used according to the invention as a combination with the compound of formula 1 include epinastine, cetirizine, azelastine, fexofenadine, levocabastine, loratadine, mizolastine, ketotifene, emedastine, dimetindene, clemastine, bamipine, hexachloropheniramine, pheniramine, doxylamine, chlorophenoxamine, dimenhydrinate, diphenhydramine, promethazine, ebastine, desloratadine, and meclizine. Preferred antiallergic agents which may be used within the scope of the present invention in combination with the compounds of formula 1 according to the invention are selected from among epinastine, cetirizine, azelastine, fexofenadine, levocabastine, loratadine, ebastine, desloratadine and mizolastine, epinastine, and desloratadine being particularly preferred. Any reference to the above-mentioned antiallergic agents also includes, within the scope of the present invention, a reference to any pharmacologically acceptable acid addition salts thereof which may exist.

Examples of PDE-IV inhibitors which may be used according to the invention as a combination with the compound of formula 1 include compounds selected from among enprofylline, roflumilast, ariflo, Bay-198004, CP-325,366, BY343, D-4396 (Sch-351591), V-11294A, and AWD-12-281. Preferred PDE-IV inhibitors are selected from among enprofylline, roflumilast, ariflo, and AWD-12-281, while AWD-12-281 is particularly preferred as the combination partner with the compound of formula 1 according to the invention. Any reference to the abovementioned PDE-IV inhibitors also includes, within the scope of the present invention, a reference to any pharmacologically acceptable acid addition salts thereof which may exist. By the physiologically acceptable acid addition salts which may be formed by the abovementioned PDE-IV inhibitors are meant, for example, pharmaceutically acceptable salts selected from among the salts of hydrochloric acid, hydrobromic acid, sulfuric acid, phosphoric acid, methanesulfonic acid, acetic acid, fumaric acid, succinic acid, lactic acid, citric acid, tartaric acid, and maleic acid. According to the invention, the salts selected from among the acetate, hydrochloride, hydrobromide, sulfate, phosphate, and methanesulfonate are preferred in this context.

Suitable preparations for administering the salts of formula 1 include, for example, tablets, capsules, suppositories, solutions, etc. The content of the pharmaceutically active compound(s) should be in the range from 0.05 to 90 wt.-%, preferably 0.1 to 50 wt.-% of the composition as a whole.

Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example, collidone or shellac, gum arabic, talc, titanium dioxide, or sugar. To achieve delayed release or prevent incompatibilities, the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g., with the addition of isotonic agents, preservatives such as p-hydroxybenzoates, or stabilizers such as alkali metal salts of ethylenediaminetetraacetic acid, optionally using emulsifiers and/or dispersants, while if water is used as diluent, for example, organic solvents may optionally be used as solubilizers or dissolving aids, and the solutions may be transferred into injection vials or ampoules or infusion bottles.

Capsules containing one or more active substances or combinations of active substances may, for example, be prepared by mixing the active substances with inert carriers such as lactose or sorbitol and packing them into gelatine capsules.

Suitable suppositories may be made, for example, by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, or chalk), synthetic mineral powders (e.g., highly dispersed silicic acid and silicates), sugars (e.g., cane sugar, lactose, and glucose), emulsifiers (e.g., lignin, spent sulfite liquors, methylcellulose, starch, and polyvinylpyrrolidone) and lubricants (e.g., magnesium stearate, talc, stearic acid, and sodium lauryl sulfate).

For oral use, the tablets may obviously contain, in addition to the carriers specified, additives such as sodium citrate, calcium carbonate, and dicalcium phosphate together with various additional substances such as starch, preferably potato starch, gelatin, and the like. Lubricants such as magnesium stearate, sodium lauryl sulfate, and talc may also be used to produce the tablets. In the case of aqueous suspensions, the active substances may be combined with various flavor enhancers or colorings in addition to the above-mentioned excipients.

For administering the compounds of formula 1 for the treatment of asthma or COPD, it is particularly preferred according to the invention to use preparations or pharmaceutical formulations which are suitable for inhalation. Inhalable preparations include inhalable powders, propellant-containing metered-dose aerosols, or propellant-free inhalable solutions. Within the scope of the present invention, the term propellant-free inhalable solutions also includes concentrates or sterile inhalable solutions ready for use. The formulations which may be used within the scope of the present invention are described in more detail in the next part of the specification The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, and maltose), oligo- and polysaccharides (e.g., dextrans), polyalcohols (e.g., sorbitol, mannitol, and xylitol), salts (e.g., sodium chloride and calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention, the excipients have a maximum average particle size of up to 250 µm, preferably between 10 µm and 150 µm, most preferably between 15 µm and 80 µm. It may sometimes seem appropriate to add finer excipient fractions with an average particle size of 1 µm to 9 µm to the excipient mentioned above. These finer excipients are also selected from the group of possible excipients listed hereinbefore. Finally, in order to prepare the inhalable powders according to the invention, micronised active substance 1, preferably with an average particle size of 0.5 µm to 10 µm, more preferably from 1 µm to 5 µm, is added to the excipient mixture. Processes for producing the inhalable powders according to the invention by grinding and micronizing and finally mixing the ingredients together are known from the prior art. The inhalable powders according to the invention may be administered using inhalers known from the prior art.

The inhalation aerosols containing propellant gas according to the invention may contain the compounds 1 dissolved in the propellant gas or in dispersed form. The compounds 1 may be contained in separate formulations or in a common formulation, in which the compounds 1 are either both dissolved, both dispersed or in each case only one component is dissolved and the other is dispersed. The propellant gases which may be used to prepare the inhalation aerosols are known from the prior art. Suitable propellant gases are selected from among hydrocarbons such as n-propane, n-butane, or isobutane and halohydrocarbons such as-halogenated alkane derivatives selected from TG134a and TG227 and mixtures thereof.

The propellant-driven inhalation aerosols may also contain other ingredients such as cosolvents, stabilizers, surfactants, antioxidants, lubricants, and pH adjusters. All these ingredients are known in the art.

The propellant-driven inhalation aerosols according to the invention mentioned above may be administered using inhalers known in the art, such as metered dose inhalers (MDIs).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume, and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulfuric acid, and/or phosphoric acid. Examples of particularly suitable organic acids include ascorbic acid, citric acid, malic acid, tartaric acid, maleic acid, succinic acid, fumaric acid, acetic acid, formic acid, and/or propionic acid. Preferred inorganic acids are hydrochloric and sulfuric acids. It is also possible to use the acids which have already formed an acid addition salt with one of the active substances. Of the organic acids, ascorbic acid, fumaric acid, and citric acid are preferred. If desired, mixtures of the above acids may be used, particularly in the case of acids which have other properties in addition to their acidifying qualities, e.g., as flavorings, antioxidants, or complexing agents, such as citric acid or ascorbic acid, for example. According to the invention, it is particularly preferred to use hydrochloric acid to adjust the pH.

If desired, the addition of edetic acid (EDTA) or one of the known salts thereof, sodium edetate, as stabilizer or complexing agent is unnecessary in these formulations. Other embodiments may contain this compound or these compounds. In a preferred embodiment, the content based on sodium edetate is less than 100 mg/100 mL, preferably less than 50 mg/100 mL, and more preferably less than 20 mg/100 mL. Generally, inhalable solutions in which the content of sodium edetate is from 0 to 10 mg/100 mL are preferred.

Co-solvents and/or other excipients may be added to the propellant-free inhalable solutions. Preferred co-solvents are those which contain hydroxyl groups or other polar groups, e.g., alcohols, particularly isopropyl alcohol, glycols, particularly propylene glycol, polyethylene glycol, polypropylene glycol, glycol ether, glycerol, polyoxyethylene alcohols, and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilizers, complexing agents, antioxidants and/or preservatives which guarantee or prolong the shelf life of the finished pharmaceutical formulation, flavorings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols, and similar vitamins and provitamins occurring in the human body.

Preservatives may be used to protect the formulation from contamination with pathogens. Suitable preservatives are those which are known in the art, particularly cetyl pyridinium chloride, benzalkonium chloride, or benzoic acid or benzoates such as sodium benzoate in the concentration known from the prior art. The preservatives mentioned above are preferably present in concentrations of up to 50 mg/100 mL, more preferably between 5 and 20 mg/100 mL.

Preferred formulations contain, in addition to the solvent water and the active substance 1, only benzalkonium chloride and sodium edetate. In another preferred embodiment, no sodium edetate is present.

The dosage of the compounds according to the invention is naturally highly dependent on the method of administration and the complaint which is being treated. When administered by inhalation, the compounds of formula 1 are characterized by a high potency even at doses in the μg range. The compounds of formula 1 may also be used effectively above the μg range. The dosage may then be in the gram range, for example.

In another aspect, the present invention relates to the abovementioned pharmaceutical formulations as such which are characterized in that they contain a compound of formula 1, particularly the abovementioned pharmaceutical formulations which can be administered by inhalation.

The following examples of formulations illustrate the present invention without restricting its scope:

Pharmaceutical Formulations

| A. Tablets | per tablet |
|---|---|
| active substance 1 | 80 mg |
| lactose | 160 mg |
| maize starch | 240 mg |
| polyvinylpyrrolidone | 15 mg |
| magnesium stearate | 5 mg |
| | 500 mg |

The finely ground active substance, lactose, and some of the maize starch are mixed together. The mixture is screened, then moistened with a solution of polyvinylpyrrolidone in water, kneaded, wet granulated, and dried. The granules, the remaining maize starch, and the magnesium stearate are screened and mixed together. The mixture is pressed into tablets of suitable shape and size.

| B. Tablets | per tablet |
|---|---|
| active substance 1 | 100 mg |
| lactose | 55 mg |
| maize starch | 170 mg |
| microcrystalline cellulose | 35 mg |
| polyvinylpyrrolidone | 15 mg |
| sodium carboxymethyl starch | 23 mg |
| magnesium stearate | 2 mg |
| | 400 mg |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

C. Ampoule Solution

| active substance 1 | 40 mg |
|---|---|
| sodium chloride | 50 mg |
| water for inj. | 5 mL |

The active substance is dissolved in water at its own pH or optionally at pH 5.5 to 6.5 and sodium chloride is added to make the solution isotonic. The resulting solution is filtered to remove pyrogens and the filtrate is transferred under aseptic conditions into ampoules which are then sterilized and heat-sealed. The ampoules contain 5 mg, 25 mg, and 50 mg of active substance.

D. Metering Aerosol

| active substance 1 | 0.01 |
|---|---|
| sorbitan trioleate | 0.1 |
| monofluorotrichloromethane and TG134a:TG227 (2:1) | to 100 |

The suspension is transferred into a conventional aerosol container with metering valve. Preferably 50 μL suspension are released on each actuation. The active substance may also be released in higher doses if desired (e.g., 0.02 wt.-%).

E. Solutions (in mg/100 mL)

| active substance 1 | 300 mg |
|---|---|
| tiotropium bromide | 50 mg |
| benzalkonium chloride | 10.0 mg |
| EDTA | 50.0 mg |
| HCl (1N) | to pH 3.4 |

This solution can be prepared in the usual way.

F. Inhalable Powder

| active substance 1 | 8 μg |
|---|---|
| tiotropium bromide monohydrate | 7 μg |
| lactose monohydrate | to 25 mg |

The inhalable powder is prepared in the usual way by mixing the individual ingredients.

What is claimed is:

1. A compound of formula 1

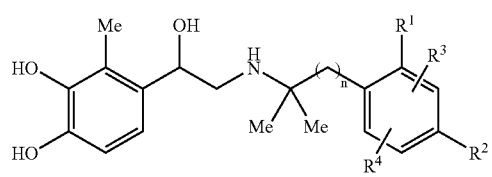

wherein:
n is 1, 2, or 3;
$R^1$ is —$C_1$–$C_4$-alkyl;
$R^3$ denotes hydrogen; and
$R^2$, and $R^4$, which are identical or different, are each —$C_1$–$C_4$-alkyl, —OH, —O—$C_1$–$C_4$-alkyl, —$C_1$–$C_4$-alkylene-halogen, —$C_1$–$C_4$-alkylene-OH, —$C_1$–$C_4$-alkylene-O—$C_1$–$C_4$-alkyl, —$CF_3$, —$CHF_2$, —$NH_2$, —NH($C_1$–$C_4$-alkyl), —N($C_1$–$C_4$-alkyl)$_2$, halogen, —COOH, —COO—$C_1$–$C_4$-alkyl, —NHCO—$C_1$–$C_4$-alkyl, —$NHSO_2$—$C_1$–$C_4$-alkyl, or —$SO_2NH_2$,
or an acid addition salt thereof.

2. The compound of formula 1 according to claim 1, wherein
n is 1 or 2;
$R^1$ is methyl or ethyl;
$R^3$ denotes hydrogen; and
$R^2$, and $R^4$, which are identical or different, are each methyl, ethyl, —OH, methoxy, ethoxy, —$CH_2F$, —$CH_2Cl$, —$CH_2Br$, —$CH_2CH_2F$, —$CH_2CH_2Cl$, —$CH_2CH_2Br$, —$CH_2OH$, —$CH_2CH_2OH$, —$CH_2$Omethyl, —$CH_2CH_2$Omethyl, —$CH_2$Oethyl, —$CH_2CH_2$Oethyl, —$CF_3$, —$CHF_2$, —$NH_2$, —NHmethyl, —NHethyl, —N(methyl)$_2$, —N(ethyl)$_2$, fluorine, chlorine, bromine, —COOH, —COOmethyl, —COOethyl, —NHCO-methyl, —NHCO-ethyl, —$NHSO_2$-methyl, or —$NHSO_2$-ethyl,
or an acid addition salt thereof.

3. The compound of formula 1 according to claim 1, wherein:
n is 1 or 2;
$R^1$ is methyl or ethyl;
$R^3$ denotes hydrogen; and
$R^2$, and $R^4$, which are identical or different, are each methyl, ethyl, —OH, methoxy, ethoxy, —$CH_2F$, —$CH_2CH_2F$, —$CH_2OH$, —$CH_2CH_2OH$, —$CH_2$Omethyl, —$CH_2CH_2$Omethyl, —$CH_2$Oethyl, —$CH_2CH_2$Oethyl, —$CF_3$, or —$CHF_2$,
or an acid addition salt thereof.

4. The compound of formula 1 according to claim 1, wherein:
n is 1 or 2;
$R^1$ is methyl or ethyl;
$R^3$ denotes hydrogen; and
$R^2$, and $R^4$, which are identical or different, are each methyl, ethyl, —OH, methoxy, ethoxy, —$CF_3$, or —$CHF_2$,
or an acid addition salt thereof.

5. The compound of formula 1 according to claim 1, wherein:
n is 1 or 2;
$R^1$ is methyl or ethyl;
$R^3$ denotes hydrogen; and
$R^2$, and $R^4$, which are identical or different, are each methyl, ethyl, —OH, or —$CF_3$,
or an acid addition salt thereof.

6. The compound of formula 1 according to claim 1, wherein:
n is 1 or 2;
$R^1$ is methyl or ethyl;
$R^3$ denotes hydrogen; and
$R^2$, and $R^4$, which are identical or different, are each methyl, or —OH,
or an acid addition salt thereof.

7. The compound of formula 1 according to claim 1, wherein n is 1, or an acid addition salt thereof.

8. The compound of formula 1 according to claim 2, wherein n is 1, or an acid addition salt thereof.

9. The compound of formula 1 according to claim 3, wherein n is 1, or an acid addition salt thereof.

10. The compound of formula 1 according to claim 4, wherein n is 1, or an acid addition salt thereof.

11. The compound of formula 1 according to claim 5, wherein n is 1, or an acid addition salt thereof.

12. The compound of formula 1 according to claim 6, wherein n is 1, or an acid addition salt thereof.

13. A pharmaceutical composition comprising an effective amount of a compound of formula 1 according to any one of claims 1 to 6 or 7 to 12 or an acid addition salt thereof and a pharmaceutically acceptable excipient or carrier.

14. A method for treatment of a disease that benefits from treatment with betamimetics in a patient, the method comprising administering to the patient in need thereof an effective amount of a compound of formula 1 according to any one of claims 1 to 6 or 7 to 12 or an acid addition salt thereof.

15. A method for the treatment of a disease or condition selected from inflammatory and obstructive respiratory complaints in a patient, the method comprising administering to a patient in need thereof an effective amount of a compound of formula 1 according to any one of claims 1 to 6 or 7 to 12 or an acid addition salt thereof.

16. The method for the treatment of asthma and/or COPD in a patient, the method comprising administering to a patient in need thereof an effective amount of a compound of formula 1 according to any one of claims 1 to 6 or 7 to 12 or an acid addition salt thereof.

* * * * *